United States Patent
Rao et al.

(10) Patent No.: US 10,272,121 B2
(45) Date of Patent: Apr. 30, 2019

(54) COMPOSITION CONTAINING AN EXTRACT OF A SEQUENTIAL OR SIMULTANEOUS FERMENTATION

(71) Applicant: ARCH PERSONAL CARE PRODUCT, LP, South Plainfield, NJ (US)

(72) Inventors: Smitha Rao, Hillsborough, NJ (US); James Vincent Gruber, Washington, NJ (US)

(73) Assignee: ARCH PERSONAL CARE PRODUCT, LP, South Plainfield, NJ (US)

(*) Notice: Subject to any disclaimer, the term of this patent is extended or adjusted under 35 U.S.C. 154(b) by 551 days.

(21) Appl. No.: 13/660,115

(22) Filed: Oct. 25, 2012

(65) Prior Publication Data

US 2013/0101576 A1  Apr. 25, 2013

Related U.S. Application Data

(60) Provisional application No. 61/550,981, filed on Oct. 25, 2011.

(51) Int. Cl.

| | | |
|---|---|---|
| *A61K 35/74* | (2015.01) | |
| *A61K 36/02* | (2006.01) | |
| *A61Q 19/08* | (2006.01) | |
| *A61K 8/99* | (2017.01) | |
| *A61K 35/744* | (2015.01) | |
| *C12P 39/00* | (2006.01) | |
| *C12N 1/20* | (2006.01) | |
| *C12P 1/00* | (2006.01) | |

(52) U.S. Cl.
CPC ........... *A61K 35/74* (2013.01); *A61K 8/99* (2013.01); *A61K 35/744* (2013.01); *A61K 36/02* (2013.01); *A61Q 19/08* (2013.01); *C12N 1/20* (2013.01); *C12P 1/00* (2013.01); *C12P 39/00* (2013.01); *A61K 2236/19* (2013.01); *A61K 2800/5922* (2013.01); *A61K 2800/85* (2013.01)

(58) Field of Classification Search
None
See application file for complete search history.

(56) References Cited

U.S. PATENT DOCUMENTS

| | | | | |
|---|---|---|---|---|
| 4,906,746 A | * | 3/1990 | Barnier | C12N 1/12 435/100 |
| 7,927,639 B2 | * | 4/2011 | Schwenninger | A01N 63/00 426/61 |
| 2004/0052759 A1 | * | 3/2004 | Sawaki et al. | 424/74 |
| 2005/0095318 A1 | * | 5/2005 | Schwenninger | A01N 63/00 426/61 |
| 2005/0196480 A1 | * | 9/2005 | Sullivan et al. | 424/780 |
| 2008/0226568 A1 | * | 9/2008 | Rozsa | A61K 8/345 424/59 |
| 2009/0004219 A1 | * | 1/2009 | Kallenmareth | A23C 15/126 424/195.17 |
| 2010/0021532 A1 | * | 1/2010 | Rao | A61K 8/06 424/450 |
| 2010/0034761 A1 | * | 2/2010 | Fenyvesi | A61Q 5/02 424/59 |
| 2010/0316720 A1 | * | 12/2010 | Stutz | A61K 8/975 424/486 |
| 2011/0052517 A1 | * | 3/2011 | Santhanam | A61K 8/64 424/62 |
| 2011/0129906 A1 | * | 6/2011 | Edelson | 435/257.1 |
| 2011/0236447 A1 | * | 9/2011 | Yoshimura | A61K 8/06 424/401 |
| 2012/0122800 A1 | * | 5/2012 | Kadushin | C12N 15/111 514/20.9 |
| 2014/0315855 A1 | * | 10/2014 | Potter | A61Q 5/006 514/59 |

FOREIGN PATENT DOCUMENTS

| | | | |
|---|---|---|---|
| EP | 0838217 A2 | | 4/1998 |
| EP | 2455450 A1 | * | 5/2012 |
| FR | 2696932 A1 | | 4/1994 |
| FR | 2725896 A1 | | 4/1996 |
| FR | 2873038 A1 | | 1/2006 |
| FR | 2912916 A1 | | 8/2008 |
| FR | 2912917 A1 | | 8/2008 |
| JP | H0987134 A | | 3/1997 |
| JP | 2006094853 A | | 4/2006 |
| JP | 2007099625 A | | 4/2007 |
| JP | 2010173991 A | | 8/2010 |
| JP | 20100173991 A | * | 12/2010 |
| RU | 2351376 A | * | 4/2009 |
| WO | WO 2006025735 A2 | * | 3/2006 |

OTHER PUBLICATIONS

Zhuojia et al. (CN 101531978 A; see English translation).*
Boekhorst et al. Microbiology (2006) 152: 3175-3183.*
Machine transation of JP 20100173991 A obtained from the JPO dated Apr. 14, 2017.*
Machine translation of RU 2351376 (published Apr. 10, 2009) downloaded from ProQuest Mar. 14, 2018 (Year: 2009).*

\* cited by examiner

*Primary Examiner* — Susan M Hanley
(74) *Attorney, Agent, or Firm* — McBee Moore Woodward & Vanik IP, LLC

(57) ABSTRACT

Disclosed herein is a topical composition that contains a fermentation extract from a simultaneous or sequential fermentation. When topically applied to skin, the composition of the invention is effective in stimulating the production of hyaluronic acid, CD44 and Caspase 14 protein in skin cells.

20 Claims, 8 Drawing Sheets
(2 of 8 Drawing Sheet(s) Filed in Color)

COMPOSITION CONTAINING AN EXTRACT OF A SEQUENTIAL OR SIMULTANEOUS FERMENTATION

CROSS-REFERENCE TO RELATED APPLICATION

This application claims priority under 35 U.S.C § 119(e) from U.S. Ser. No. 61/550,981 filed Oct. 25, 2011. The disclosure of U.S. Ser. No. 61/550,981 is incorporated herein by reference in its entirety.

FIELD OF INVENTION

The present invention relates to a composition suitable for use in personal care and therapeutic applications, and more specifically to such compositions containing dual fermentation extracts.

BACKGROUND OF THE INVENTION

Extracts derived from the fermentation of a single organism such as *Saccharomyces* sp. or *lactobacillus* sp. are known and have been used in topical compositions. Recently, it has been suggested in U.S. Patent Application Publication No. 2010/0021532, that fermentation of an organism together with plant derived polyphenols has been disclosed as a method to produce metabolites that have beneficial effects to the skin.

The use of multi-starter culture organisms and the concept of co-culturing multiple microbes have been explored within the food industry, particularly in the process of wine-making, see for example, Toro M. E et. al., *World Journal of Microbiology and Biotechnology* 18:347-354. (2002) and Herrero M. et al., *Journal of Industrial Microbiology and Biotechnology* 22:48-51 (1999). It is suggested that the taste and biochemical profiles of multi-starter wine may be superior to that of single culture inoculations as microbial interactions during multi-starter microbial wine making is critical for impacting the enhanced flavor, Clani M. et al., *International Journal of Food Microbiology* 108:239-245 (2006). However, the use of multi-start cultures for personal care products is not suggested.

Recently, the use of yeast and its derivatives has become very popular in cosmetic applications. This is driven by the fact that yeast, being eukaryotic, has similar cellular biological processes to human cells and is known to trigger the production of beneficial proteins under stress. There is also considerable historical evidence for the use of yeast derivatives and their benefits in topical skin applications by the increase in oxygen uptake. For example, U.S. Pat. No. 4,540,571 discloses yeast derivatives that improve cutaneous respiration. Yeast cell derivatives are also reported to stimulate the production of collagen and elastin in skin cells.

Recent studies suggest that yeast cell extracts have the ability to promote 'growth factors' that stimulates wound healing. For example, U.S. Pat. No. 7,217,417 discloses a method that incorporates yeast cell derivatives into a gel-based formulation for wound healing.

The use of simultaneous or sequential fermentation extracts to derive new actives has not been suggested in the art.

SUMMARY OF THE INVENTION

In one aspect, the present invention provides topical composition containing a fermentation extract removed from a simultaneous or sequential fermentation of at least two organisms.

In another aspect, provided is a topical composition containing a fermentation extract removed from a simultaneous or sequential fermentation of at least two organisms, a preservative in an amount sufficient to provide sterilizing or biostatic effect on the fermentation extract and a dermatologically acceptable vehicle.

An exemplary topical composition provided by the present invention contains a dual fermentation extract of first organism which is Propionibacteraceae *shermanii* and a second organism, which is *Lactobacillus plantarum*.

Another exemplary topical composition provided by the present invention contains a dual fermentation extract of first organism which is micro-algae and a second organism, which is *Lactobacillus plantarum*.

Also provided is a method for preparing the fermentation extract which contains the process steps of growing a first organism to a late-logarithmic growth phase using a first chemically defined nutrient media to produce a second nutrient media containing the first organism and secondary metabolite expressions from the first organism; contacting the second nutrient media with a second organism; allowing the first organism and the second organism to be fermented simultaneously in a second nutrient media in order to produce a fermented mixture containing a water soluble portion and a water insoluble portion; separating the water insoluble portion from the fermented mixture, thereby isolating the water soluble portion and producing the dual fermentation extract.

In another aspect of the present invention is a method for stimulating the production of hyaluronic acid and CD44 in skin cells, by applying the topical composition to the skin of a user in need of treatment with a topical composition containing a dual fermentation extract.

In another aspect of the present invention is a method for stimulating the production of hyaluronic acid and Caspase-14 in skin cells, by applying the topical composition to the skin of a user in need of treatment with a topical composition containing a dual fermentation extract.

These and other aspects will become apparent when reading the detailed description of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6B illustrates hyaluronic acid expression from in vitro stratum corneum disruption model treated with Retinol.

FIG. 6C illustrates hyaluronic acid expression from in vitro stratum corneum disruption model treated a dual fermentation extract derived from simultaneous fermentation of Lactobacillaceae and micro-algae

DETAILED DESCRIPTION OF THE PREFERRED EMBODIMENTS

Figure 1:
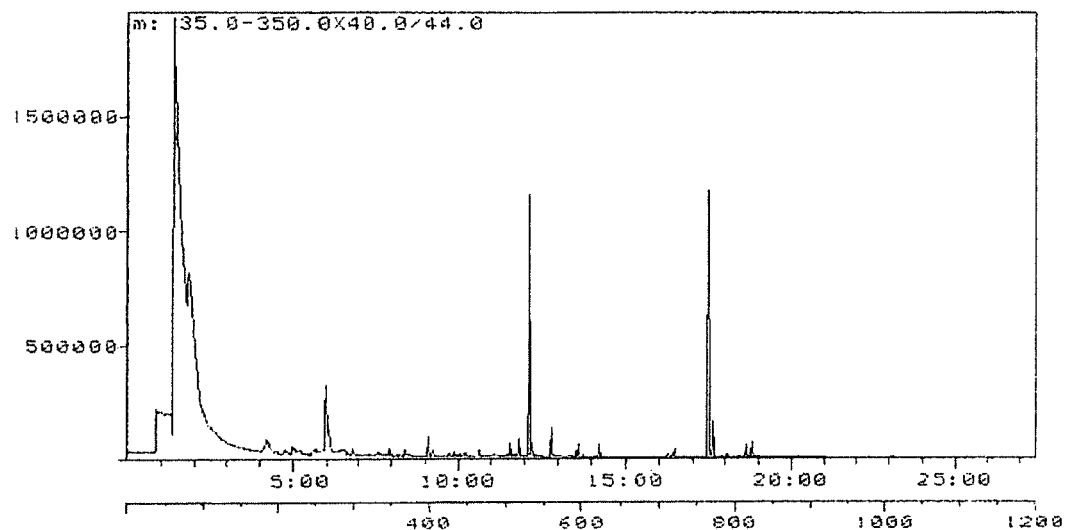
FIG. 1 is a GC-MS spectrum of Lactobacillaceae fermentation extract for comparative purposes.

It has now been surprisingly found that topical compositions containing a fermentation extract removed from a simultaneous or sequential fermentation of at least two organisms has beneficial properties in topical compositions for personal care and therapeutic applications. The beneficial properties include, for example, when a composition containing the fermentation extract is topically applied to the skin, it has been discovered that the composition is effective in stimulating the production of hyaluronic acid, CD44 and Caspase 14 protein in skin cells.

Without being bound by any theory, it is believed that simultaneous or sequential fermentation causes one organism to become competitive with another organism. The environment of competition for a second organism in the presence of metabolites from a first organism causes the second organism to begin expressing metabolites that allow it to flourish in the competitive environment. In particular, the second organism may metabolize the secondary metabolites and cytokines from the first organism or visa-versa. In this way, the ferment extract becomes a new composition that contains unique metabolic actives that would not otherwise be available when the organisms are fermented individually.

To make the fermentation extract of the present invention, in one embodiment, a first organism is allowed to grow in a chemically defined nutrient media. As used herein, "chemically defined nutrient media" is defined as a media that contains specific chemical sources of nutrients for organism growth, for example chemical sources for nitrogen, carbon, etc. Chemically defined nutrient media generally does not contain biological sources of nutrients such as yeast or animal/plant tissue nutrients. The first organism modifies the nutrient media by the expression of secondary metabolites. Secondary metabolites include proteins, cytokines, polysaccharides, nucleic acids and the like. Then a second organism can be inoculated into the modified nutrient media containing the first organism and metabolites from the first organism. The first organism and the second organism then are allowed to be fermented simultaneously in the modified nutrient media in order to produce a fermented mixture. Alternatively, the second organism is allowed to be fermented in the modified nutrient media after the fermentation of the first organism. Generally, the fermentation will contain a water soluble portion and a water insoluble portion. The water insoluble portion can be removed from the fermented mixture, thereby isolating the water soluble portion, which is fermentation extract of the invention. As used herein, "water soluble" is defined as 1 gram of dual fermentation extract dissolving into 1 gram of water. The extracts may also be soluble in water/organic solvent mixtures such as, but not limited to, aqueous glycols and aqueous glycerols.

A "fermentation extract" as used herein, refers to a composition derived from a fermentation of two or more organisms. The fermentation extract of the invention contains cytoplasmic and extra-cellular components from both organisms including, but not limited to, the nutrient broth, cellular protein material, cellular nucleic material, cellular protoplasmic material and/or cell wall components and the like.

When two organisms are grown simultaneously or sequentially, the process is referred to herein as a "dual fermentation". The fermentation extract from a dual fermentation is referred to herein as a "dual fermentation extract". As described herein, the examples are directed to dual fermentation for preparing a dual fermentation extract; however, it is contemplated that additional organisms may be fermented simultaneously or sequentially.

Generally, to produce a dual fermentation extract, a first organism is allowed to grow in a growth media to a late-logarithmic phase. As used herein, "late logarithmic phase" is defined as the last phrase of exponential growth for organism cultures. Exponential growth is characterized by exponential cell growth or doubling. The duration of exponential growth is dependent on the population of organisms present at a given time and the availability of nutrients in the media. Typically, the first organism is allowed to grow until the optical density at 600 nm is at least about 6. The first organism is allowed to grow at a set temperature range for a set period of time. The resulting modified nutrient media is collected in a sterile transfer tank. The modified nutrient media can be further purified to remove the first microbe. Alternatively, the first organism can be allowed to remain in the modified media during addition of a second organism such as *Lactobacillus* sp. Growth of the second organism is monitored by changes in optical density and viable counts (optical density at 600 nm is at least 6; or viable counts of about $10^9$ colony forming units/ml).

Essentially any nutrient media may be used in the present invention and is not particularly limited. Nutrient media are known to those skilled in the art and formation of nutrient media useful for the present invention is not particularly limited. Typical nutrient media can be found, for example, in the "Handbook of Microbiological Media" published by CRC Press (Boca Raton, Fla.), which is incorporated herein by reference in its entirety. For example, a suitable nutrient media for use in the fermentation process of the invention is a chemically defined media, without any animal-derived products, and with well-defined and adequate sources of carbon, nitrogen and phosphorus.

During the fermentation, fed-batch cultures are typically grown at approximately 20-30° C., in a nutrient media supplemented with carbon sources (glycerol, lactose); nitrogen sources (peptides and amino-acids) and phosphorous. The pH is typically kept constant at 5.0±1.5 by titration with 2M NH$_4$OH. The fermentation oxygen conditions are constantly monitored by a sterilizable oxygen probe and the fermentation atmosphere is typically maintained by minimal stirring in the fermenter with a maximum velocity between 100 and 150 rpm. The nitrogen feed rate is typically set at 0.01-0.5 VVM (volume air/vessel volume/per minute). Other gases may or may not be employed and additional external stress may or may not be applied such as, for example, use of oxidative stress enhancing techniques such as addition of ozone or UV light or stress related techniques such as, for example, heat.

The fermentation process can be carried out in any type of stirred or wave-type bio-reactor. Examples of useful bioreactors for the present invention include, but are not limited to, batch-fed reactors available from New Brunswick Scientific (Edison, N.J.) or Applikon Biotechnology (Foster City, Calif.).

Both the first and the second organisms can be grown in aerobic or anaerobic conditions or in combinations of aerobic and anaerobic conditions for stimulation of secondary metabolites. Optionally, during the fermentation process, the organisms can be exposed to stressors, for example, chemicals such as hydrogen peroxide and ozone, energies such as ultra-sound, UV, infrared radiation or heat.

Measurement of secondary metabolites can be done using techniques known to those skilled in the art. One particularly effective technique includes chromatography combined with mass spectroscopy (LC/MS or GC/MS). Another effective method to measure secondary metabolites is through the use of commercially available organism genomic arrays. Such arrays are well known to those skilled in the art and arrays for organisms such as *Saccharomyces* and *Lactobacillus* are available commercially. Other methods for measuring secondary metabolite expression may include flow cytometry. Secondary metabolite expression may be measured using gas chromatography and mass spectroscopy (GC/MS). Examples of such instruments include instruments from Skyray Instrument Inc. and Thermo-Scientific Inc.

The fermentation extract can be obtained by separating the bio-mass and extracting active ingredients from the extra-cellular secretions of the first and the second organisms. Alternatively, the cells can be lysed to obtain the dual fermentation extract lysate by processes known to those skilled in the art. In these processes, the cell walls are ruptured by chemical, enzymatic or physical means or by a combination of these. The dual fermentation extract may be further purified by any number of means known to those skilled in the art, including but not limited to, chromatography, solvent extraction, centrifugation, decantation, filtration or carbon treatment. The dual fermentation extract can be further concentrated by any means known to those skilled in the art, including but not limited to, evaporation, spray-drying, lyophylization, belt or drum drying.

Suitable microbes/organisms for the simultaneous or sequential fermentation of the present invention can include various microbial families and genera, known to those skilled in the art including, but not limited to: *Neurospora, Ceratostomella, Claviceps, Xylaria, Rosellinia, Helotium, Sclerotinia, Tulostoma, Rhizopogon, Truncocolumella, Mucor, Rhizopus, Entomophthora, Dictostylium, Blastocladia, Synchytrium, Saprolegnia, Peronospora, Albugo, Pythium, Craterellus, Ptetygellus, Phytophthora, Plasmodiophora, Tuber, Hydnum, Lecanora, Roccella, Pertusaria, Usnea, Evernia, Ramalina, Alectoria, Cladonia, Parmelia, Cetraria, Agaricus, Cantharellus, Omphalotus, Coprinus, Lactarius, Marasmius, Pleurotus, Pholiota, Russula, Lactarius, Stropharia, Entoloma*, Lepiotaceae, *Corticium, Pellicularia, Tricholoma, Volvaria, Clitocybe, Flammulina, Saccharomyces, Schizosaccharomyces, Eurotium, Aspergillus, Thielavia, Peziza, Plectania, Morchella, Wynnea, Helvella, Gyromitra, Phallales, Dictyophera, Mutinus, Clathrus, Pseudocolus, Lycoperdon, Calvatia, Geastrum, Radiigera, Astreus, Nidularia, Gastrocybe, Macowanites, Gastroboletus, Albatrellus, Neolentinus, Nigroporus, Oligoporus, Polyporus, Fistulina, Fomes, Boletus, Fuscoboletinus, Leccinum, Phylloporus, Sufflus, Strobilomyces, Boletellus, Tremella, Auricularia, Dacrymyces, Melampsora, Cronartium, Puccinia, Gymnosporangium, Tilletia, Urocystis, Septobasidium, Hygrocybe, Hygrophorus, Hygrotrama, Neohygrophorus, Cortinarius, Gymnopilus, Trichophyton, Microsporum, Monilia, Candida, Cercosporella, Penicillium, Blastomyces, Cercospora, Ustilaginoidea, Tubercularia, Fusarium, Rhizoctinia, Ozonium, Sclerotium, Geoglossum*, or *Armfflaria*; Nocardioidaceae, *Aeromicrobium; Friedmanniella, Kribbella, Marmoricola; Micropruina, Nocardioides, Pimelobacter, Propionicicella, Propionicimonas, Thermasporomyces, Brooklawnia, Luteococcus, Propionibacterium, Propionimicrobium, Lactobacillus, Sharpea, Ambispora, Acaulospora, Enthrophosphora, Abortiporus, Amylocystis, Antrodia, Antrodiella, Aurantiporus, Auriporia, Buglossoporus, Ceriporia, Ceriporiopsis, Cerrena, Criolopsis, Cryptoporus, Daedalea, Daedaleopsis, Dantronia, Diplomitoporus, Donkioporia, Fomitopsis, Hapalopilus, Laetiporus, Laeptoporus, Megasporoporia, Melanoporia, Meripilus, Nigroporus, Oligoporus, Ossicaulis, Oxyporus, Parmastomyces, Pilatoporus, Piptoporus, Poria, Postia, Rigidoporus, Taiwanofungus, Tinctoporellus, Trametes, Tyromyces, Wolfiporia, Palaeococcus, Pyrococcus, Thermococcus, Byssochlamys, Chaetosartorya, Chromocleista, Dichotomomyces, Edyuillia, Emericella, Erythrogymnotheca, Eupenicillium, Eurotium, Fenneffia, Hamigera, Hemicarpenteles, Neopetromyces, Neosartorya, Penicifﬁopsis, Petromyces, Segenoma, Talaromyces, Thermoascus, Thrichocoma, Warcupiella, Aspergillus, Merimbla, Paecilomyces, Phialosimplex, Sagenomella, Septofusidium, Thysanophora, Geosmithia*, Lactobacillaceae Propionibacterineae, *Actinomycetales Malasezzia*, micro-algae and other similar species. It should also be appreciated that prokaryotes, algal cells, plant cells, animal cells or insect cells may also be co-fermented with one or more microbes mentioned above. Of the above, microbes/organisms *Saccharomyces, Schizosaccharomyces, Propionicicella, Propionicimonas, Thermasporomyces*, Propionibacteriaceae, *Propionimicrobium*, Lactobacillaceae, *Hapalopilus*, Coriolaceae, Mitosporic Trichocomaceae, Malasseziaceae, Lactobacillaceae Propionibacterineae, *Actinomycetales* and micro-algae are of particular interest.

In one embodiment, microbial cultures belonging to the family of Lactobacillaceae and Propionibacteriaceae are used to produce the dual fermentation extract. Methods for growing *Lactobacillus* and Propionibacteria individually are known to those skilled in art. Typically, bacteria belonging to the phylum Lactobacillaceae and Propionibacteriaceae are either obligate anaerobes or micro-aerophilic; that is they prefer to be grown in the absence of oxygen. Some species can tolerate the presence of small amounts of oxygen.

To produce a dual fermentation extract, the first organism, for example, Propionibacteraceae sp. is allowed to grow in a growth media to a late-logarithmic phase. Advantageously, the first organism is allowed to grow until the optical density at 600 nm is at least 6. In one embodiment, the first organism is allowed to grow between 25° C. to 30° C. for about 16 to about 18 hours. The resulting modified nutrient media was collected in a sterile transfer tank. The modified nutrient media can be further purified to remove the first microbe. Alternatively, the first organism can be allowed to remain in the modified media during addition of a second organism such as *Lactobacillus* sp. Growth of the second organism is monitored by changes in optical density and viable counts (optical density at 600 nm is at least 6; or viable counts of $10^9$ colony forming units/ml).

In another embodiment, cultures belonging to the family of micro-algae *Ulkenia* sp. and Lactobacillaceae are used to produce the dual fermentation extract. Methods for growing *Ulkenia* and *Lactobacillus* individually are known to those skilled in art. Typically, bacteria belonging to the phylum *Ulkenia* and Lactobacillaceae are either obligate aerobes or micro-aerophilic; and prefer to be grown in nutrient rich medium with mineral salts.

To produce a dual fermentation extract, the first organism, for example, micro-algae sp. is allowed to grow in a growth media to a late-logarithmic phase. In one embodiment, the first organism is allowed to grow between 20° C. to 24° C. for about 96 to about 388 hours. The resulting modified nutrient media is collected in a sterile transfer tank. The modified nutrient media can be further purified to remove the first organism. Alternatively, the first organism can be allowed to remain in the modified media during addition of a second organism such as *Lactobacillus* sp. Growth of the second organism is monitored by changes in optical density and viable counts (optical density at 600 nm is at least 6; or viable counts of $10^9$ colony forming units/ml).

The dual fermentation extract can be encapsulated using techniques known to those skilled in the art including, but not limited to, forming liposomes or other lipid encapsulants, spray drying the dual fermentation extract, encapsulating the dual fermentation extract in a polymer capsule, absorbing or adsorbing the dual fermentation extract onto an inert substrate and the like.

The dual fermentation extract may be used in topical compositions. Such topical compositions may provide skin cells with protection by the secondary metabolite expression that is not expressed during the microbial fermentation of individual organisms. By the application of topical compositions containing dual fermentation extract, it is likely to provide anti-aging, skin whitening, skin cell turnover, skin cell protection, skin barrier protection, skin hydration and other therapeutic benefits.

The topical composition of the present invention may contain the fermentation extract in an amount of between about 0.01 wt % up to about 10 wt %, based on the weight of the topical composition. Generally, the topical composition may contain between about 0.1 wt % and 5 wt % of the fermentation extract, typically between about 0.5 wt % to about 2 wt % based on the weight of the topical composition.

In addition to the fermentation extract, the topical composition may advantageously contain a preservative. A preservative may be added to the fermentation extract or topical composition to maintain the environment of the fermentation extract and to protect the fermentation extract against contamination by undesirable airborne organisms. As used herein, a "preservative" is defined as an ingredient that renders the fermentation extract sterile or biostatic to undesirable organisms. Preservatives include acids, alcohols, glycols, parabens, quaternary-nitrogen containing compounds, isothiazolinones, aldehyde-releasing compounds and halogenated compounds and enzymes. Illustrative alcohols include phenoxyethanol, isopropyl alcohol, and benzyl alcohol; illustrative glycols include propylene, butylene and pentylene glycols; illustrative parabens include (also known as parahydroxybenzoic acids) methyl, propyl and butyl parabens; illustrative quaternary nitrogen containing compounds include benzalkonium chloride, Quaternium 15; illustrative isothiazoles include methylisothiazoline, methylchlorolisothiazoline; illustrative aldehyde releasing agents include DMDM hydantoin, imidazolidinyl urea and diazolidinyl urea; illustrative anti-oxidants include butylated hydroxytoluene, tocopherol and illustrative halogenated compounds include triclosan and chlorhexidine digluconate. Illustrative enzymes include glucose oxidase and lactoperoxidase. Examples of preservatives useful for the purpose of the present invention can be found in Steinberg, D. "Frequency of Use of Preservatives 2007". Cosmet. Toilet. 117, 41-44 (2002) and, "Preservative Encyclopedia" Cosmet. Toilet. 117, 80-96 (2002). In addition, enzyme preservative systems such as those described in the article by Ciccognani D. Cosmetic Preservation Using Enzymes. in "Cosmetic and Drug Microbiology", Orth DS ed., Francis & Taylor, Boca Raton, Fla. (2006) can also be effective for use in the topical composition.

Generally, the preservative will be present in an amount of at least about 0.01 wt %, advantageously, at least about 0.1 wt %, up to about 10 wt % of the total weight of the topical composition. Typically, the least amount of the preservative need is used and the preservative is typically present in an amount of less than about 5 wt % and more typically in the range of about 0.1 wt % to about 2.0 wt % based on the weight of the topical composition.

Topical compositions may also contain a dermatologically-acceptable carrier. As used herein, the phrase "dermatologically-acceptable carrier", means that the carrier is suitable for topical application to the skin, hair, nails and the like which has good aesthetic properties, is compatible with the fermentation extract and any other components, and will not cause any untoward safety or toxicity concerns. Dermatologically-acceptable carriers are also generally cosmetically and/or pharmaceutically acceptable as well.

The dermatologically-acceptable carrier or "carrier" can be in a wide variety of forms. For example, emulsion carriers, including, but not limited to, oil-in-water, water-in-oil, water-in-oil-in-water, and oil-in-water-in-silicone emulsions, are useful herein. These emulsions can cover a broad range of viscosities, e.g., from about 100 cps to about 200,000 cps. These emulsions can also be delivered in the form of sprays using either mechanical pump containers or pressurized aerosol containers using conventional propellants. These carriers can also be delivered in the form of a mousse. Other suitable topical carriers include anhydrous liquid solvents such as oils, alcohols, and silicones (e.g., mineral oil, ethanol, isopropanol, dimethicone, cyclomethicone, and the like); aqueous-based single phase liquid solvents (e.g., hydro-alcoholic solvent systems); and thickened versions of these anhydrous and aqueous-based single phase solvents (e.g., where the viscosity of the solvent has been increased to form a solid or semi-solid by the addition of appropriate gums, resins, waxes, polymers, salts, and the like). Examples of topical carrier systems useful in the present invention are described in the following four references all of which are incorporated herein by reference in their entirety: "Sun Products Formulary" Cosmetics & Toiletries, vol. 105, pp. 122-139 (December 1990); "Sun Products Formulary", Cosmetics & Toiletries, vol. 102, pp. 117-136 (March 1987); U.S. Pat. No. 4,960,764 to Figueroa et al., issued Oct. 2, 1990; and U.S. Pat. No. 4,254,105 to Fukuda et al., issued Mar. 3, 1981.

The carriers can comprise from about 50 wt % to about 99 wt % by weight of the topical compositions, and will generally be present in an amount from about 75 wt % to about 99 wt %, based on the total weight of the topical composition. Typically, the carrier will make up from about 85 wt % to about 95 wt % of the total weight of the composition.

Exemplary carriers include hydro-alcoholic systems and oil-in-water emulsions. When the carrier is a hydro-alcoholic system, the carrier can comprise from about 0% to about 99% of ethanol, isopropanol, or mixtures thereof, and from about 1% to about 99% of water. More preferred is a carrier containing from about 5% to about 60% of ethanol, isopropanol, or mixtures thereof, and from about 40% to about 95% of water. Especially preferred is a carrier containing from about 20% to about 50% of ethanol, isopropanol, or mixtures thereof, and from about 50% to about 80% of water. When the carrier is an oil-in-water emulsion, the carrier can include any of the common excipient ingredients for preparing these emulsions. A more detailed discussion of suitable carriers is found in U.S. Pat. No. 5,605,894 to Blank et al., and, U.S. Pat. No. 5,681,852 to Bissett, both of which are herein incorporated by reference in their entirety.

The topical composition may optionally contain other functional ingredients such as, water, surfactants, emulsifiers, conditioners, emollients, waxes, oils, polymers, thickeners, fixatives, colorants, humectants, moisturizers, stabilizers, diluents, solvents and fragrances. In addition the personal care composition may contain active ingredients such as botanicals, nutraceuticals, cosmeceuticals, therapeutics, pharmaceuticals, antifungals, antimicrobials, steroidal hormones, antidandruff agents, anti-acne components, sunscreens, preservatives and the like.

The topical composition containing the fermentation extract can be used in various types of cosmetic formulations including, but not limited to lotions, ointments, creams, sprays, spritzes, aqueous or aqueous-alcoholic mixture gels, mousses, patches, pads, masks, moistened clothes, wipes, solid sticks, clear sticks, lip sticks, aerosol creams, anhydrous powders, talcs, tonics, oils, emulsions and bath salts. Such cosmetic formulations may be used as a topical application on the skin.

According to another embodiment of the present invention, also provided is a composition concentrate containing (a) a fermentation extract; (b) a preservative present in an amount sufficient to provide sterilizing and biostatic effect on component (a), wherein component (a) is present in an amount of from about 90% to about 99.9% by weight of the composition, and component (b) is present in an amount of from 0.1% to 10% by weight of the composition. Generally, the fermentation extract is between about 98% to about 99.5% by weight of the composition, and component (b) is present in an amount of from 0.5% to 2% by weight of the composition. Other additional ingredients, such as solvent or carrier may also be present in the concentrate.

The following examples are intended to illustrate, but in no way limit the scope of the present invention. All parts and percentages are by weight and all temperatures are in degrees Celsius unless explicitly stated otherwise.

EXAMPLES

Example 1

Organism and Media

Bacterial cell cultures were isolated from whey powdered extracts. For the purpose of the present invention, microbial cultures belonging to the family of Lactobacillaceae and Propionibacteriaceae are especially preferred. The choice of the first microbe (Lactobacillaceae vs. Propionibacteriaceae) strictly depends on the growth rate. Propionibacteriaceae was chosen for its faster growth rate as the desire was to metabolize and enrich most of the primary ingredients in the media. For the purposes of this invention, the two microbes were grown anaerobically or under micro-aerophilic conditions (no oxygen or limited oxygen). Stock cultures were maintained on media containing tryptone; yeast extract; filtered whey extract (pH 7.0); and agar (Sigma St. Louis, Mo.). The parent stock culture was grown in shaker flasks with media comprising of yeast extract 10%; tryptic soy broth 5%, potassium phosphate 2.5%; di-potassium phosphate 1.5%; lactose 10%; glycerol 5% (Sigma St. Louis, Mo.). In addition to the media ingredients, supplemental growth factors such as amino-acids, vitamin blends and minerals were added to the growth media (Sigma, St. Louis, Mo.). Antifoam sigma-emulsion B was used throughout the process (Sigma, St. Louis, Mo.).

Bioreactor

After optimization of treatment via the shake flask trials, the process was scaled up to 2 L and 15 L fermentation stages (2 L New Brunswick Scientific, Edison N.J. and 15 L Applikon Biotechnology Foster City Calif.). Both microbes were grown in anaerobic conditions and the oxygen concentration was monitored by dissolved oxygen monitors. Nitrogen gas was sparged in the bio-reactor to control the level of oxygen and for the expression of secondary metabolites. The anaerobic conditions were constantly monitored by a sterilizable DO probe and the anaerobic atmosphere was maintained by minimal stirring in the fermentor with a maximum velocity between 100 and 150 rpm. The nitrogen rate was set at 0.01-0.5 µM (volume air/vessel volume/per minute). To produce a dual fermentation extract of the present invention, *Propionibacterium shermanii* cell culture was grown between 25° C. to 30° C.; most preferably grown at 27° C. For the purposes of this invention, the two microbes were grown simultaneously in the fermenter (The second microbe *Lactobacillus plantarum* was grown in the presence of the first microbe). The *Lactobacillus plantarum* was inoculated at a particular time point (16-18 hours after inoculation of the first microbe; with Optical Density 600 nm≥5) during the fermentation process, when the nutrient media was limiting; thereby causing competition for nutrients in a closed environment. The impact of introducing the second microbe *Lactobacillus plantarum* at a nutrient limited stage elicits a competitive, 'survival type' response between the two microbes, particularly when grown in a closed system such as a bioreactor. The media was continuously monitored for growth and depletion of nutrients (by online monitoring, optical density measurements). Stress was induced by nutrient limitation and oxygen deprivation of the first microbe, before the introduction of the second microbe.

The final dual fermentation extract was obtained by separating the bio-mass and extracting active ingredients from the extra-cellular secretions of the dual microbes. The dual fermentation extract can be further purified by filtration. The dual fermentation extract can be further concentrated by means of selective molecular weight membrane filtration known to those skilled in the art. The final concentration of the dual ferment extract in the aqueous media is at least 0.01%. More preferably, the concentration of the dual fermentation extract is at least 0.1%. Phenoxyethanol was used as a preservative at a concentration of 0.5-1.1% (Sigma St. Louis, Mo.).

The two individual organism controls (Lactobacillaceae vs. Propionibacteriaceae) were grown under identical conditions as described above. The distinguishing parameter for microbial control samples is the absence of the second microbe and the absence of elicitation of secondary metabolites. The individual organisms extract were purified using the above mentioned selective molecular weight membrane filtration techniques.

Example 2: Metabolite Analysis by GC/MS

Figure 2:
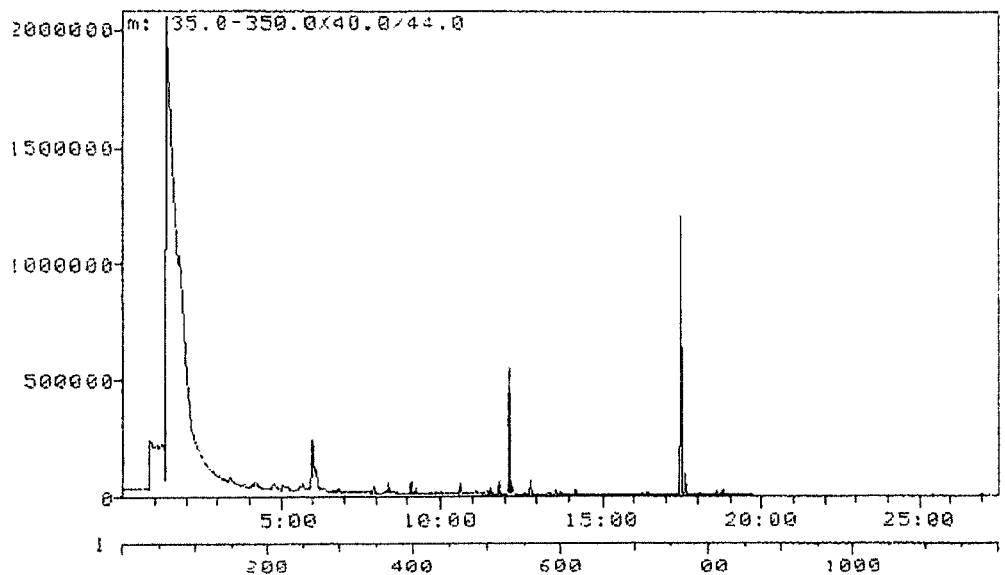
FIG. 2 is GC-MS spectrum of Propionibacteriaceae fermentation extract for comparative purposes.
Figure 3:
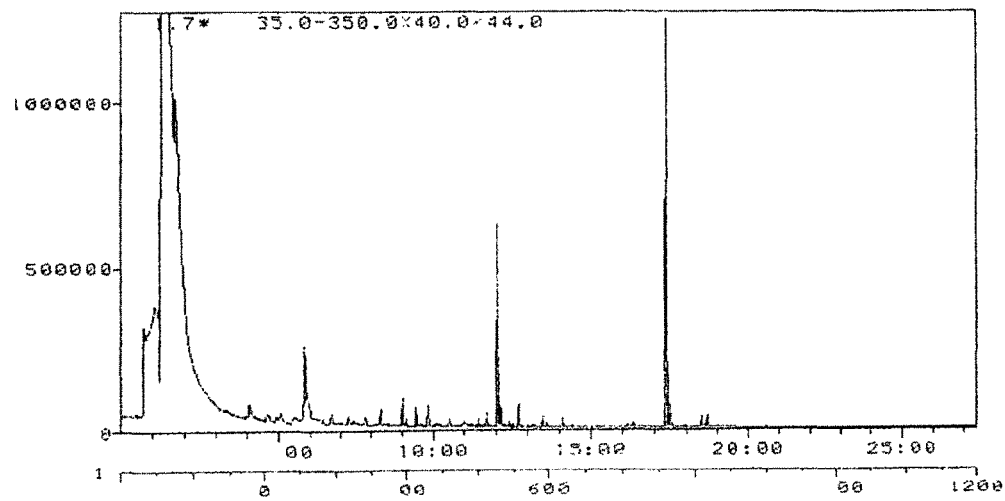
FIG. 3 is a GC-MS spectrum of a dual fermentation extract derived from simultaneous fermentation of Lactobacillaceae and Propionibacteriaceae.

After completion of the dual fermentation from example 1, GC-MS was conducted to analyze the expression of different metabolites. Three samples were analyzed as shown below:

Fermentation control 1—Lactobacillaceae
Fermentation control 2—Propionibacteriaceae
Dual Fermentation Extract Aqueous samples (1, 2, and 3) were subjected to acid-specific extraction; where the acid fraction was isolated, methylated with diazomethane reagent and the organic acids were analyzed by GC-MS as their corresponding methyl esters. Test samples were directly injected into GC and the low molecular weight acids were also analyzed by volatile component head space analysis (headspace GC-MS). FIGS. 1 and 2 are GC-MS analysis of microbe 1 and microbe 2 which are control samples. FIG. 3 represents the GC-MS analysis of dual fermentation extract, which indicates that the competition of two microbes induces the expression of new metabolites that are otherwise not expressed (if the microbes are grown individually).

Example 3 Human Skin Cell Microarray Analyses

The dual fermentation product made as described in Example 1 was examined for its influence on two skin cell lines, fibroblasts and keratinocytes, using human genomic microarrays (Agilent Technologies). The cells were treated with 1% of the dual ferment from Example 1 for 24 hrs. The resulting treated skin cells were centrifuged and the pellet containing nuclear material was re-suspended in RNA Later (Ambion) and stored at 4° C. Total RNA from the human cells was extracted using a RiboPure RNA extraction kit (Ambion), and mRNA was subsequently amplified using a Message AMP aRNA Kit (Ambion). For the array, samples of aRNA were fluorescently labeled with either Cy-3 or Cy-5 using a MicroMax array labeling kit (Perkin Elmer). Labeled aRNA was then applied to a skin cell DNA Microarray chip for epidermal fibroblasts and keratinocytes and hybridized overnight (Agilent Technologies). On the following day the chips were washed and scanned with an Axon 4100A DNA microarray scanner and analyzed using Axon Genepix-Pro® software. The method employed for gene microarray analysis can be found in United States Patent Application Publication No. US2006/0110815.

The genes of interest obtained from the human epidermal keratinocytes and human dermal fibroblasts gene-microarray were screened for genes related to specific important skin functions. The up-regulation (ratio of media >1.3) or down-regulation (ratio of media <0.7) of several genes involved in various skin metabolism functions was analyzed. For the purpose of gene microarray analysis, the term "up-regulation" or "up-regulated" implies that the gene is over-expressing RNA. The term "down-regulation" or "down-regulated" implies RNA is being under-expressed. The results are reported in Table 1.

TABLE 1

DNA micro-array analysis of human epidermal keratinocytes and human dermal fibroblasts treated with 1% of the dual ferment extract from example 1.

| Gene Name | NHEF | NHEK | Description |
| --- | --- | --- | --- |
| ABCB6 | 1.36 | 1.79 | ABCB6 ATP-binding cassette |
| AGK | | 1.405 | Acylglycerol kinase (mitochondrial) |
| ATP5A1 | 1.356 | 1.611 | ATP synthase, H+ transporting, mitochondrial F1 complex, alpha subunit 1 |
| GAPDH | 1.562 | 1.649 | Glyceraldehyde-3-phosphate dehydrogenase |
| GLRX2 | 1.519 | 1.409 | Glutaredoxin 2 |
| MTCH1 | 1.534 | | Mitochondrial carrier homolog 1 |
| MRPL27 | 1.402 | 1.523 | mitochondrial ribosomal protein L27 |
| TIMM23 | | 1.333 | TIMM23 translocase of inner mitochondrial membrane 23 homolog |
| TOMM22 | | 1.507 | Translocase of outer mitochondrial membrane 22 homolog |
| ALOX5 | 1.375 | 1.548 | ALOX5 arachidonate 5-lipoxygenase |
| DHCR7 | 2.724 | 1.628 | 7-dehydrocholesterol reductase |
| HMGCR | 2.426 | | 3-Hydroxy 3-methylglutaryl-coenzyme A reductase (rate limiting step for cholesterol synthesis |
| LSS | 1.456 | | Lanosterol synthase |
| LSS | 1.569 | 1.37 | Lanosterol synthase |
| MVK | 1.915 | | Mevalonate kinase |
| MVK | 1.595 | | Mevalonate kinase |
| MVD | 2.75 | 1.706 | Mevalonate pyrophosphate decarboxylase |
| LIAS | | 1.568 | Lipoic acid synthetase |
| SQLE | 2.006 | | Squaleneepoxidase |
| PPARA | | 2 | PPARG peroxisome proliferator-activated receptor gamma, adipicyte differentiation |
| AQP1 | | 1.5 | Aquaporin 1 |
| AQP3 | 1.377 | 1.926 | Aquaporin 3 |
| CD44 | 1.401 | 1.606 | Transmembrane glycoprotein CD44 (receptor for HLA, COL and MMP) |
| HAS1 | 2 | 1.5 | Hyaluronan synthase 1 |
| TYRP1 | 3 | 3 | Tyrosinase related peptide 1 |
| MC1R | | 1.667 | melanocortin 1 receptor |

TABLE 1-continued

DNA micro-array analysis of human epidermal keratinocytes and human dermal fibroblasts treated with 1% of the dual ferment extract from example 1.

| Gene Name | NHEF | NHEK | Description |
|---|---|---|---|
| MC1R | | 1.333 | melanocortin 1 receptor |
| HAMP | 1.313 | 1.407 | hepcidin antimicrobial peptide |
| ARPC1A | 1.381 | | Actin related protein 2/3 complex 1A |
| ARPC3 | 1.378 | 1.662 | Actin related protein 2/3 complex subunit 3 |
| CCS | 1.414 | 1.508 | Copper chaperone for SOD |
| COL1A2 | 2.115 | 0.565 | Collagen Type I |
| CDH1; HCT1 | 2.8 | 2.25 | Cadherin 1 Calcium dependent proteins (cell adhesion, with tissues) |
| HSPA1A | 1.39 | 1.306 | Heat shock 70 kDa protein 1A |
| HSPA5 | 1.695 | | Heat shock 70 kDa protein (folding protein in ER) |
| HSPB1 | | 2.426 | Heat shock 70 kDa protein (expressed env. stress) |
| HYOU1 | 1.316 | | Heat shock 70 kDa protein (expressed env. stress) |
| FGF1 | 2 | | fibroblast growth factor |
| ITGA6 | | 1.355 | Integrin, alpha 6 |
| ITGA5 | 1.989 | | lntegrin, alpha 5 |
| IVL | 3.429 | 1.576 | Involucrin |
| KL | 3 | 6 | Klotho |
| KLB | | 1.385 | klotho beta |
| LAD1 | 1.421 | | Ladinin 1; basement membrane - epithelia cells |
| LAMC2 | 1.915 | 2.483 | Laminin, beta 2 (laminin S) ECM glyco-proetin |
| TGFA | 1.75 | 1.304 | Transforming growth factor, alpha |
| TIMP2 | | 1.315 | TIMP metallopeptidase inhibitor 2 |
| TIMP4 | 0.695 | 1.5 | TIMP metallopeptidase inhibitor 4 |
| MMP1 | 2.095 | 0.44 | matrix metallopeptidase 1 (interstitial collagenase) |
| CYP51A1 | 1.672 | | Cytochrome P450 46 |
| BCL2 | | 3 | Homo sapiens B-Cell CLL/Lymphoma 2 |
| BCL2L1 | 1.358 | 1.117 | BCL2-related protein A1 |
| CLOCK | 1.286 | 1.367 | Circadian Rhythm |
| MTNR1A | 1.043 | 1.361 | Melatonin receptor 1, alpha |
| RARA | | 1.369 | Retinoic acid receptor, alpha |
| RARG | | 1.587 | Retinoic acid receptor, gamma |
| RXRA | 1.352 | | Retinoid X receptor, alpha |
| CRABP2 | | 1.404 | Cellular retinoic acid binding protein 1 |
| SOD2 | 1.491 | | superoxide dismutase 1, Mictochondrial |
| SOD3 | 1.446 | 1.711 | superoxide dismutase 3, extracellular |
| PRDX1 | 1.59 | 1.54 | Peroxiredoxin 1 |
| PRDX5 | 1.542 | 1.617 | Peroxiredoxin 1 |
| RAD23A | | 1.444 | RAD23 homolog B |
| GPX1 | | 1.315 | Glutathione peroxidase 1 (H1O2 peroxidation) |
| GPX5 | 1.652 | | Glutathione peroxidase 1 (H1O2 peroxidation) |
| UNG | 1.57 | 1.391 | Uracil-DNA glycosylase |
| USF1 | | 1.5 | Upstream transcription factor 1 |
| CYGB | 2 | | Cytoglobin |
| LIG1 | | 1.409 | DNA ligase 1 |
| OXSR1 | 2.038 | 2.505 | Oxidative stress responsive 1 |
| FN1 | | 1.419 | Fibronectin 1 |
| DEFB4 | 1.327 | 1.711 | Defensin, beta |
| FLG | 2.5 | 1.4 | Filaggrin |
| GRN | 2.372 | 1.806 | Granulin |
| PLOD3 | 2.024 | 2.022 | Lysine hydroxylase 3 (CHO in collagen) |
| IKBKAP | 0.5 | 0.545 | IKBKAP inhibitor of kappa light polypeptide gene enhancer in B-cells, kinase complex-associated protein |
| IL1A | 0.667 | | interleukin 1, alpha |

Example 4 Full Thickness Evaluations Comparing Individual Organism Ferment Extracts Against the Dual Ferment from Example 1

The dual fermentation extract of example 1 was tested on the MatTek® full thickness skin tissue model against the microbial controls (SNA1380A and SNA1380B) of example 1. This skin model consists of highly differentiated keratinocytes grown on a collagen matrix embedded with fibroblasts. Upon arrival, the tissues were stored at 4° C. until used. For use, the tissues were removed from the agarose-shipping tray and placed into a 6-well plate containing 4 ml of assay medium and allowed to equilibrate overnight at 37±2° C. and 5±1% CO2. After the overnight equilibration, the media was replaced with 4 ml of fresh media and 50 µl of test material was then applied topically to the tissues. The tissues were then incubated for 24 hours at 37±2° C. and 5±1% CO2. The following samples from Example 1 were evaluated on MatTek® full thickness skin tissues:

1. Untreated
2. SNA1380A—Fermentation Control 1—Lactobacillaceae (Treatments 1% & 2%)
3. SNA1380B—Fermentation Control 1—Propionibacteriaceae (Treatments 1% & 2%)
4. SNA1380C—Dual Fermentation extract (Treatments 1% and 2%)

CD44 and HAS1 Assays

Figure 4:
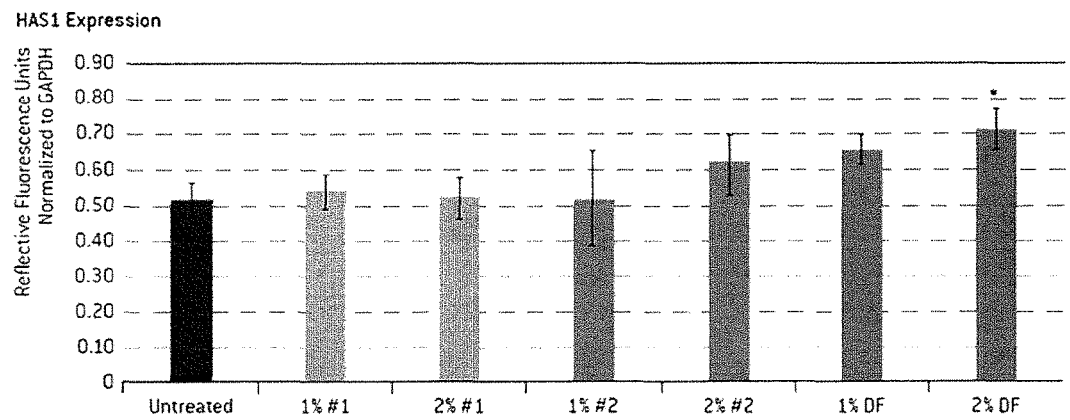
FIG. 4 illustrates HAS1 expression from full thickness tissues treated with Lactobacillaceae fermentation extract, Propionibacteriaceae fermentation extract, and a dual fermentation extract derived from simultaneous fermentation of Lactobacillaceae and Propionibacteriaceae.
Figure 5:
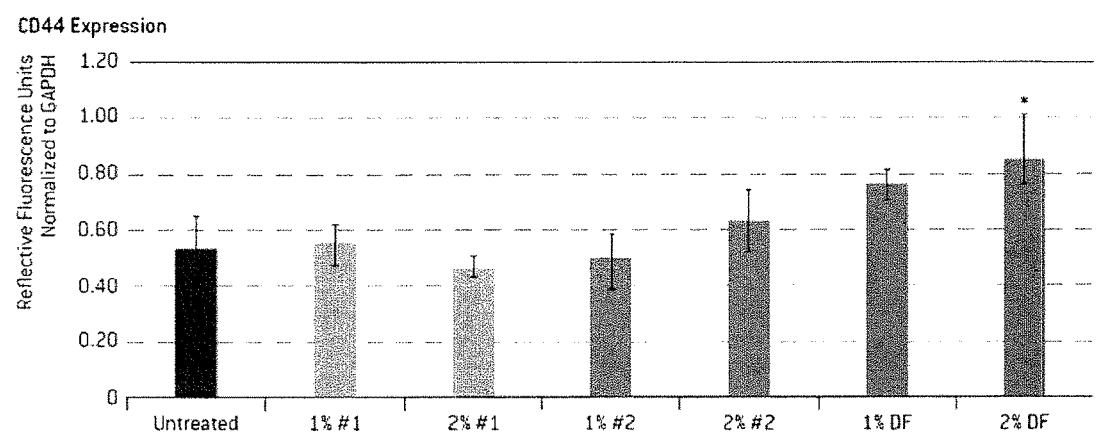
FIG. 5 illustrates CD44 expression from full thickness tissues treated with Lactobacillaceae fermentation extract, Propionibacteriaceae fermentation extract, and a dual fermentation extract derived from simultaneous fermentation of Lactobacillaceae and Propionibacteriaceae.

A membrane was equilibrated in Tris Buffered Saline (TBS: 20 mM Tris, pH 7.5, 150 mM NaCl) and assembled into a Bio-Dot microfiltration apparatus. After assembly, 200 µl of TBS was added to each well used in the Bio-Dot and the vacuum was applied to ensure that there was adequate flow through all of the wells. Next, each tissue homogenate sample (approximately 10 μg) was assigned a well in the apparatus and was applied to the appropriate well. The samples were filtered under low vacuum. TBS was added to wells not assigned a sample to ensure that the membrane did not dry out during the procedure. At the end of the blotting procedure an additional 200 μl of TBS was applied and filtered through each well. The membrane was then removed from the Bio-Dot apparatus, washed in TBS for 5-10 minutes and then placed into blocking solution (Tris Buffered Saline [20 mM Tris, pH 7.5, 150 mM NaCl, 1% non-fat milk powder) and allowed to incubate for at least 1 hour at room temperature on a rocking platform. The results of the assay are shown in FIGS. 4 and 5.

Results from the full thickness tissue evaluation indicate that the dual ferment of Example-1 (SNA-1380C) shows statistically significant up-regulation of HAS1 protein compared to the untreated control at 1% and 2%. The individual control samples did not show statistical significance compared to untreated controls. The results are graphically shown in FIG. 4.

Results from the full thickness tissue evaluation indicate that the ferment of Example-1 (SNA-1380C) shows statistically significant up-regulation of CD44 protein compared to the untreated control at 1% and 2%. The individual control samples did not show statistical significance compared to untreated controls. The results are graphically shown in FIG. 5.

Example 5—Dual Ferment of Micro-Algae and Lactobacillaceae

A dual fermentation process was commenced the competitive fermentation of micro-algae and bacterial cell cultures. Micro-algae and bacterial cultures are Lonza proprietary strains. For the purpose of the present invention, microorganisms are micro-algae cultures belonging to the family of *Thraustochytrids* and bacteria belonging to the family Lactobacillaceae are especially preferred. The choice of the first microbe (micro-algae vs. Lactobacillaceae) strictly depended on the growth rate. Micro-algae was chosen for its slower growth rate as the desire was to metabolize and enrich most of the primary ingredients in the media. For the purposes of this invention, the two organisms were grown aerobically. Stock cultures were maintained on media containing tryptone; yeast extract; filtered whey extract (pH 7.0); and agar (Sigma St. Louis, Mo.). The parent stock culture was grown in shaker flasks with media comprising of $NaNO_3$ (25%), $CaCl_2 \cdot 2H_2O$ (2.5%), $MgSO_4 \cdot 7H_2O$ (7.5%), $K_2HPO_4$ (7.5%), $KH_2PO_4$ (17.5%), NaCl (2.5%), KOH (31%), $FeSO_4 \cdot 7H_2O$ (4.98%), $H_2SO_4$ (1%) and $H_3BO_3$ (11.42%). In addition to the media ingredients, supplemental growth factors such as amino-acids, vitamin blends and minerals were added to the growth media (Sigma, St. Louis, Mo.). Antifoam sigma-emulsion B was used throughout the process (Sigma, St. Louis, Mo.).

Bioreactor

After optimization of treatment via the shake flask trials, the process was scaled up to 2 L and 15 L fermentation stages (2 L New Brunswick Scientific, Edison N.J. and 15 L Applikon Biotechnology Foster City Calif.). The micro-algae was grown in an carbon dioxide rich environment. Air was sparged in the bio-reactor to control the level of carbon dioxide and for the expression of secondary metabolites. The conditions were constantly monitored by a sterilizable DO probe and the atmosphere was maintained by agitation of the cells and media with a maximum velocity between 250-600 rpm. The air rate was set at 1.0-2.0 VVM (volume air/vessel volume/per minute). To produce a dual fermentation extract of the present invention, *Ulkenia* sp. culture was grown between 20° C. to 24° C.; most preferably grown at 21° C. For the purposes of this invention, the two organisms were grown simultaneously in the fermenter (The second microbe *Lactobacillus plantarum* was grown in the presence of the first microbe). The *Lactobacillus plantarum* was inoculated at a particular time point (96-388 hours after inoculation of the first organism) during the fermentation process, when the nutrient media was limiting; thereby causing competition for nutrients in a closed environment. The impact of introducing the second microbe *Lactobacillus plantarum* at a nutrient limited stage elicits a competitive, 'survival type' response between the two organisms, particularly when grown in a closed system such as a bioreactor. The media was continuously monitored for growth and depletion of nutrients (by online monitoring, optical density measurements). Stress was induced by nutrient limitation and carbon dioxide deprivation of the first organism, before the introduction of the second microbe.

The final dual fermentation extract was obtained by separating the bio-mass and extracting active ingredients from the extra-cellular secretions of the two organisms. The dual fermentation extract may be further purified by filtration. The dual fermentation extract can be further concentrated by means of selective molecular weight membrane filtration known to those skilled in the art. The final concentration of the dual ferment extract in the aqueous media is at least 0.01%. More preferably, the concentration of the dual fermentation extract is at least 0.1%. Phenoxyethanol was used as a preservative at a concentration of 0.5-1.1% (Sigma St. Louis, Mo.).

Example 6—In Vitro Evaluations Comparing Individual Organism Ferment Extracts Against the Dual Ferment from Example 5 on In Vitro Stratum Corneum Disruption Model The dual fermentation extract of example 5 was evaluated for histological changes on the MatTek® full thickness skin tissue model from example 5. This skin model consists of highly differentiated keratinocytes grown on a collagen matrix embedded with fibroblasts and were maintained as described in Example 4. On the following day, a 4 mm biopsy punch was used to wound the tissue by removing just the epidermal layer of the tissues. After the tissues were wounded 100 μl of fresh test material was applied to the tissues in the morning and afternoon for two consecutive days. Prior to applying new test material the old test material was removed and the tissues were rinsed once with 100 μl of PBS. After the tissues were wounded 100 μl of fresh test material was applied to the tissues in the morning and afternoon for seven consecutive days. Prior to applying new test material the old test material was removed and the tissues were rinsed once with 100 μl of PBS and the tissues were incubated in between applications.

At the end of the treatment time, the tissue was fixed in fixed in Histochoice MB for three hours. The tissues were then processed, embedded in paraffin wax and sectioned 5 μm and fixed. The slides were then probed using either a primary antibody or with biotinylated hyaluronic acid binding protein and stained for specific protein activity. Tissues were viewed using a fluorescence microscope equipped with a QiClick imaging camera. Microscopic images were then captured using QCapture software.

The following samples from Example 5 were evaluated with the in vitro stratum corneum disruption model:
1. Untreated
2. Retinol 50 nm
3. Dual ferment from example 5 at 2%

Caspase 14 and Hyaluronic Acid Assays

Figure 6A:
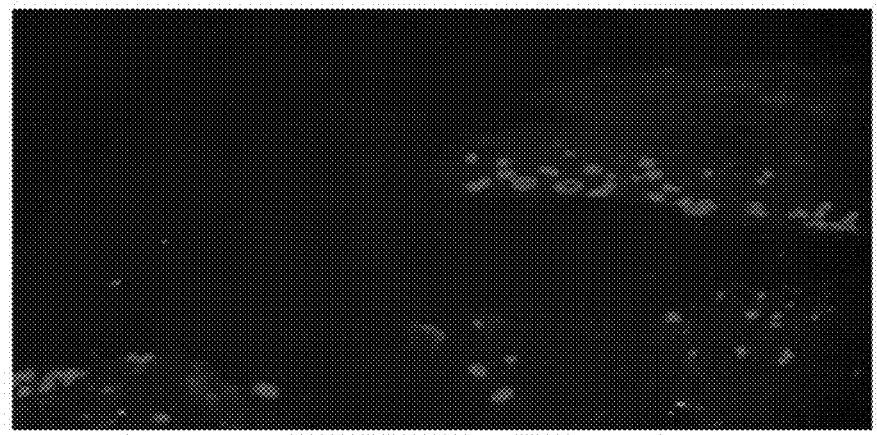
FIGS. 6A, 6B and 6C each illustrates hyaluronic acid expression from in vitro stratum corneum disruption model which is untreated.
Figure 6B:
Figure 6C:
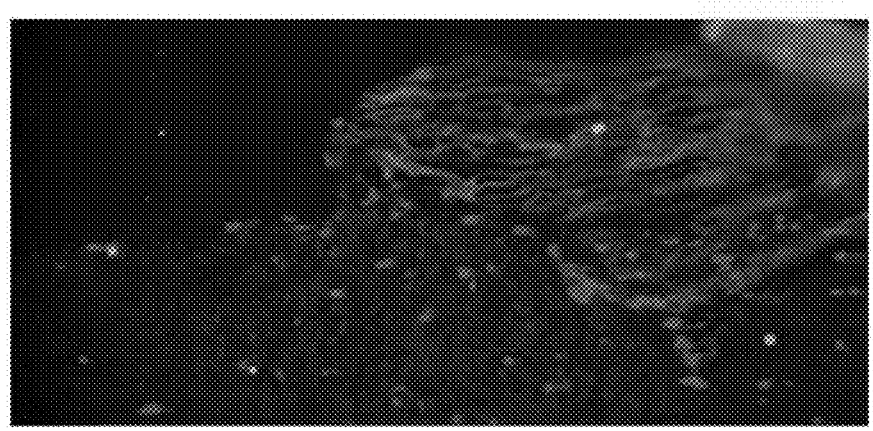
Figure 7A:
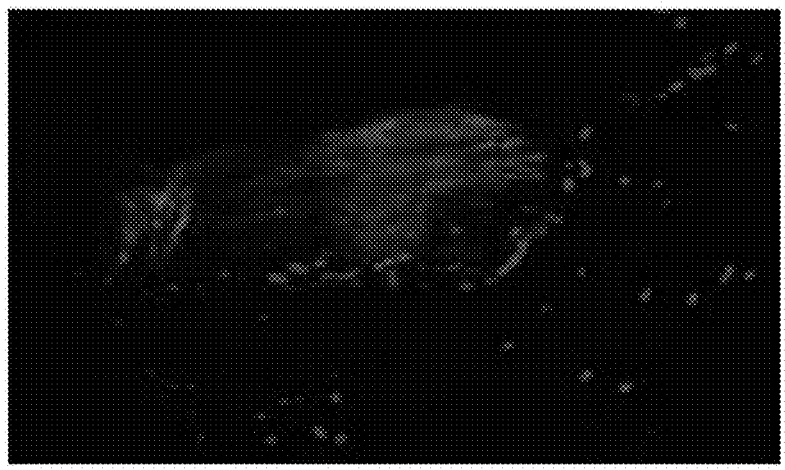
FIG. 7A illustrates Caspase-14 expression from in vitro stratum corneum disruption model treated which is untreated.
Figure 7B:
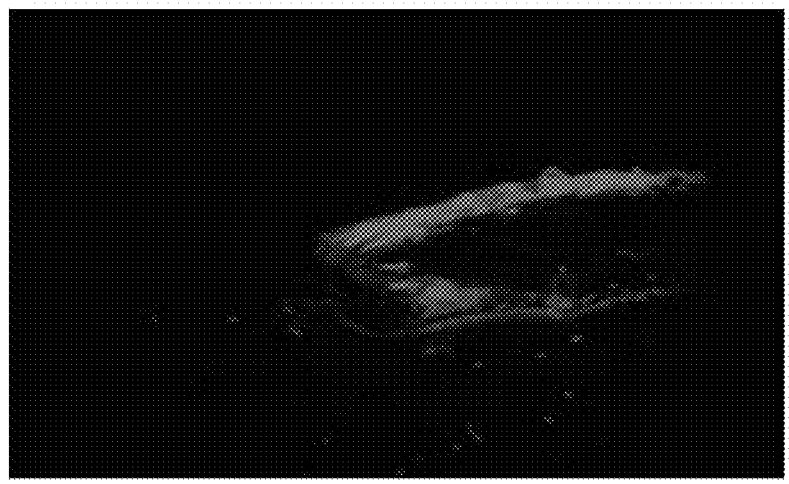
FIG. 7B illustrates Caspase-14 expression from in vitro stratum corneum disruption model treated with Retinol
Figure 7C:
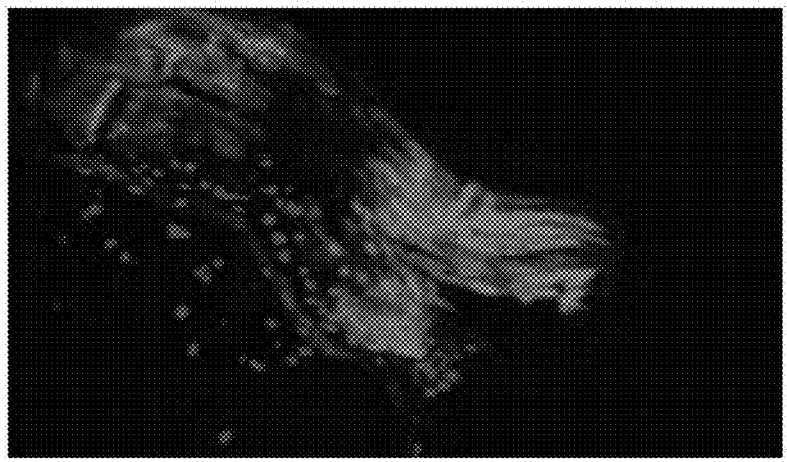
FIG. 7C illustrates Caspase-14 expression from in vitro stratum corneum disruption model treated with a dual fermentation extract derived from simultaneous fermentation of Lactobacillaceae and micro-algae

The histological images are presented in FIGS. 6A, 6B, and 6C and FIGS. 7A, 7B, and 7C, with a treatment description and an explanation as follows. The images from the hyaluronic acid evaluation are shown in FIGS. 6A, 6B and 6C (hyaluronic acid is selectively stained and show in the Figures as the light areas). While the images from the caspase-14 study is shown in FIGS. 7A, 7B and 7C (Caspase-14 selectively stained and are shown as the light areas). The images were obtained at the edge of the wound such that the edge of the epidermis at the wound site, the opening of the wound and the dermal layer below are all visible. Hyaluronic acid in FIGS. 6A, 6B and 6C and caspase-14 in FIGS. 7A, 7B and 7C are shown as the lights areas along the leading edge of the wound epidermis. The small white dots are cells.

Results from the in vitro stratum corneum disruption model indicate that the dual ferment of Example 5 shows statistically significant up-regulation of hyaluronic acid protein, shown in FIG. 6C as compared to the untreated control, shown FIG. 6A and positive control of retinol, shown in FIG. 6B. Results from the in vitro stratum corneum disruption model indicate that the dual ferment of Example-5 shows statistically significant up-regulation of Caspase-14 protein, shown in FIG. 7A, as compared to the untreated control, shown in FIG. 7A and positive control of retinol, as shown in FIG. 7C. In both studies, the individual control samples did not show statistical significance compared to untreated controls.

Example 7—In Vivo Evaluation of Dual Ferment Extract from Example 5 for Anti-Aging Benefits A single-blind clinical evaluation and comparison of the efficacy of dual ferment from example 5 was evaluated in a facial skin care product versus placebo. The study was conducted for duration of 60 days with the facial product applied twice a day. The study was initiated after a wash-out period of 7 days, and results were captured at day 0, day 30 and day 60. The treatment groups are indicated as follows:
1. Test Product A: Placebo (example A)
2. Test Product B: 2% dual ferment from example 5

Figure 8A:
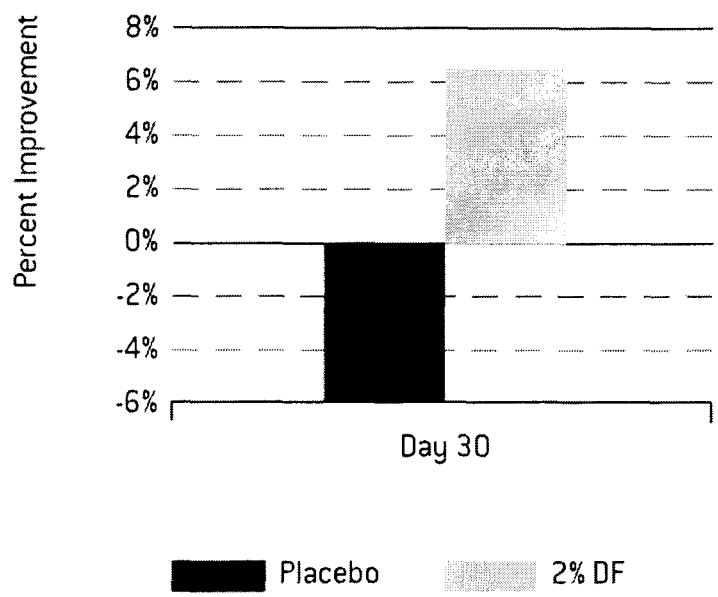
FIGS. 8A and 8B show In vivo evaluation of skin elasticity via cutometer by the application of micro-algae and *lactobacillus* dual ferment.
Figure 8B:
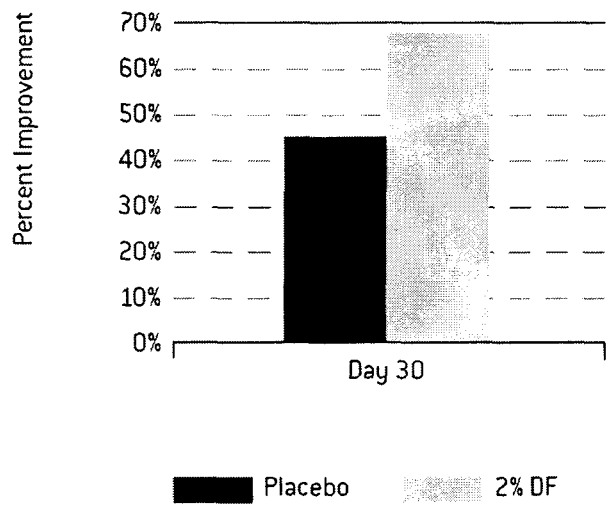
Figure 9A:
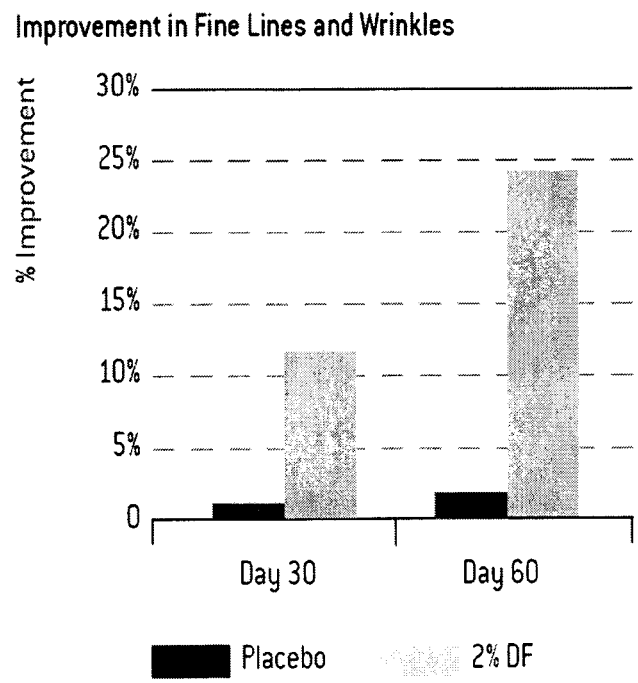
FIGS. 9A and 9B show In vivo evaluation of fine lines and wrinkles by the application of micro-algae and *lactobacillus* dual ferment.
Figure 9B:
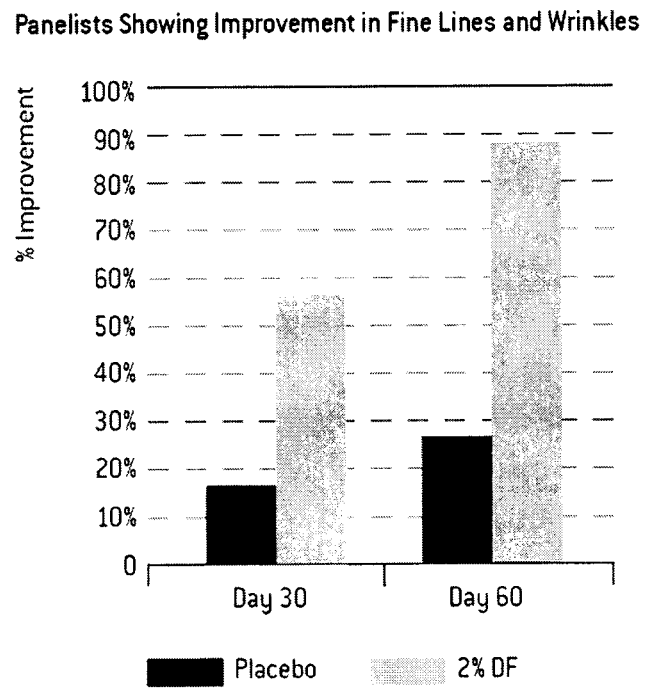
Figure 10A:
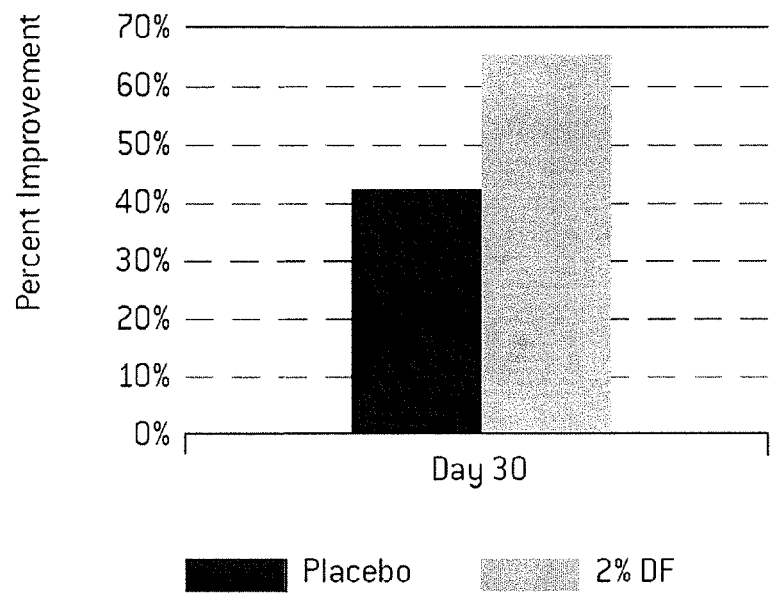
FIGS. 10A and 10B show In vivo Silflo evaluation of fine lines and wrinkles in the periocular region by the application of micro-algae and *lactobacillus* dual ferment.
Figure 10B:
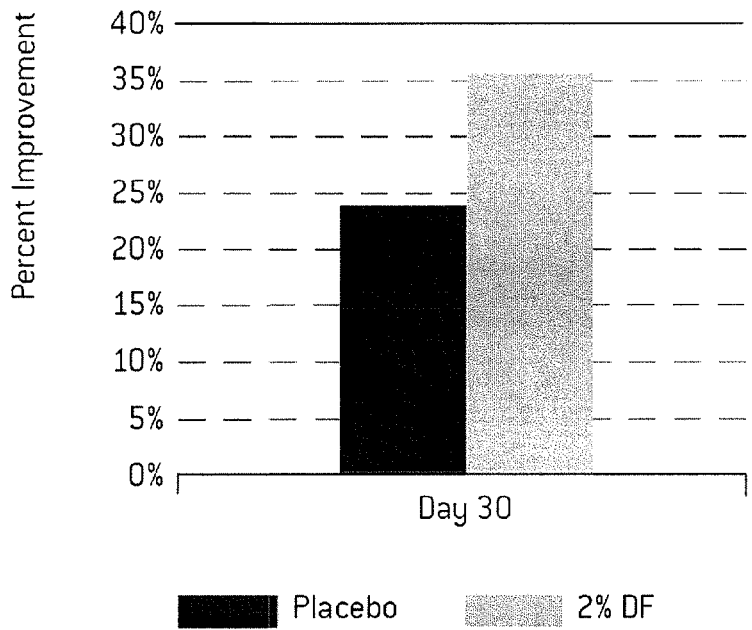

Several criteria were evaluated in vivo including cutometer for quantitative measurement of skin elasticity, silicone replicas for quantitative assessment of fine lines and wrinkles and protection of skin barrier function. Dual ferment at 2% by weight from example 5 showed a statistically significant improvement in skin elasticity compared to placebo, as shown in FIG. 8. In addition, dual ferment from example 5 showed a statistically significant improvement in fine lines and wrinkles as shown in FIGS. 9A and 9B. Silicone replicas in the periocular region also indicate that the application topical application of dual ferment from example 5 shows a statistically significant improvement in fine lines and wrinkles, as is shown in FIGS. 10A and 10B.

The following are examples of skin care compositions which may be prepared in accordance with the present invention using the dual fermentation extract as prepared using example-1.

Example Composition A

The example below shows a composition which may be made having a high internal phase water-in-oil emulsion incorporating the dual fermentation extract prepared as disclosed in Example 1 by blending the components in Table A.

TABLE A

| Ingredient | Wt % |
|---|---|
| 1,3-dimethyl-2-imidazolidione | 0.2 |
| Polyoxylene (2) oleyl ether | 5.0 |
| Bentone 38 | 0.5 |
| MgSO4•7H2O | 0.3 |
| Preservative[1] | 0.5 |
| Dual fermentation extract | 2.0 |
| Water | To 100 |

[1]DMDM Hydantoin

Example Composition B

The example below shows a composition which may be made having an oil-in-water cream consistency, incorporating the dual fermentation extract prepared as disclosed in Example 1 by blending the components in Table B.

TABLE B

| Ingredient | Wt % |
|---|---|
| Mineral Oil | 4 |
| 1,3-dimethyl-2-imidazolidione | 1 |
| Cetyl Alcohol POE (10)[1] | 4 |
| Cetyl Alcohol | 4 |
| Triethanolamine | 0.75 |
| Butane 1,3-diol | 3 |
| Xanthum Gum | 0.3 |
| Methyl, Propyl, and Butyl Paraben | 0.5 |
| Dual fermentation extract | 2.0 |
| Water | To 100 |

Example Composition C

The example below shows a composition which will be an alcoholic lotion incorporating the dual fermentation extract prepared as disclosed in Example 1, which may be prepared by blending the components in Table C.

TABLE C

| Ingredient | Wt % |
|---|---|
| 1,3-dimethyl-2-imidazolidione | 0.3 |
| Ethanol | 40 |
| Dual fermentation extract | 0.5 |
| Water | To 100 |

Example D

The example below shows a composition which will be a sub-micron emulsion concentrate that contains the dual fermentation extract prepared as disclosed in Example 1 and which may be prepared by blending the components in Table D

TABLE D

| Ingredient | Wt % |
|---|---|
| TrimethylopropaneTricaprylate/Tricaprate | 18.0 |
| Glycerin | 8.0 |

TABLE D-continued

| Ingredient | Wt % |
| --- | --- |
| Cetcaryl alcohol | 2.0 |
| Cetcareth 20 | 2.0 |
| Glyceral stearate | 2.0 |
| BHT | 0.5 |
| Dual fermentation extract | 1.5 |
| Water | To 100 |

Example E

The example below shows an aqueous composition which that contains the dual fermentation extract prepared as disclosed in Example 1 and which may be prepared by blending the components in Table E.

TABLE E

| Ingredient | Wt % |
| --- | --- |
| Water | 97 |
| Dual fermentation extract | 2 |
| Preservative | 1 |

While the invention has been described above with references to specific embodiments thereof, it is apparent that many changes, modifications and variations can be made without departing from the invention concept disclosed herein. Accordingly, it is intended to embrace all such changes, modifications, and variations that fall within the spirit and broad scope of the appended claims.

What is claimed is:

1. A topical composition comprising:
    a fermentation extract,
    a preservative in an amount sufficient to provide sterilizing or biostatic effect on the fermentation extract, and
    a dermatologically acceptable vehicle,
    wherein said preservative is selected from the group consisting of an acid, an alcohol, a glycol, a paraben, a quaternary-nitrogen containing compound, an isothiazolinone, an aldehyde-releasing compound, a halogenated compound, and an enzyme,
    wherein the fermentation extract consists of extra-cellular secretions separated from a simultaneous fermentation of two organisms grown simultaneously in the same fermenter, a first organism selected from the group consisting of the family Propionibacteriaceae and micro-algae, wherein the micro-algae is selected from the group consisting of *Thraustochytrid* and *Ulkenia* sp., and a second organism of the family Lactobacillaceae,
    wherein the composition comprises between about 0.1 wt % and about 10 wt % of the fermentation extract, between about 0.1 wt % and about 10 wt % of the preservative and between about 50 wt % and 95 wt % of the dermatologically acceptable vehicle.

2. The topical composition according to claim 1, wherein the first organism is micro-algae selected from the group consisting of *Thraustochytrid* and *Ulkenia* sp.

3. The topical composition according to claim 1, wherein the first organism is Propionibacteriaceae.

4. The topical composition of claim 1, wherein the first organism is Propionibacteriaceae *shermanii* and the second organism is *Lactobacillus plantarum*.

5. A method for stimulating the production of hyaluronic acid and CD44 in skin cells comprising contacting skin of a subject with the topical composition according to claim 4.

6. A method for stimulating the production of hyaluronic acid and Caspase-14 in skin cells comprising contacting skin of a subject with the topical composition according to claim 4.

7. The topical composition of claim 1, wherein the first organism is micro-algae selected from the group consisting of *Thraustochytrid* and *Ulkenia* sp. and the second organism is *Lactobacillus plantarum*.

8. A method for stimulating the production of hyaluronic acid and CD44 in skin cells comprising contacting skin of a subject with the topical composition according to claim 5.

9. A method for stimulating the production of hyaluronic acid and Caspase-14 in skin cells comprising contacting skin of a subject with the topical composition according to claim 5.

10. The topical composition of claim 1, wherein the preservative is selected from the group consisting of salicylic acid, sorbic acid, phenoxyethanol, benzyl alcohol, ethanol, Quaternium-15, glucose oxidase and lactoperoxidase in combination with a substrate, and combinations thereof.

11. The topical composition according to claim 10, wherein the preservative is phenoxyethanol.

12. The topical composition of claim 10, wherein the preservative is present in an amount of about 0.1 wt % based on the total weight of the composition.

13. The topical composition of claim 1, further comprising at least one ingredient selected from the group comprising water, surfactants, emulsifiers, conditioners, emollients, waxes, oils, polymers, thickeners, fixatives, colorants, humectants, moisturizers, stabilizers, diluents, solvents, fragrances, botanicals, nutraceuticals, cosmeceuticals, therapeutics, pharmaceuticals, antifungals, antimicrobials, steroidal hormones, antidandruff agents, anti-acne components, sunscreens, and combinations thereof.

14. The topical composition according to claim 1, wherein the fermentation extract is produced by a simultaneous fermentation process comprising the steps of:
    (i) growing the first organism to a late-logarithmic growth phase using a first chemically defined nutrient media to produce a second nutrient media containing the first organism and secondary extracellular metabolites expressed from the first organism;
    (ii) contacting the second nutrient media with the second organism;
    (iii) allowing the first organism and the second organism to be fermented simultaneously in the second nutrient media in order to produce a fermented mixture containing a water soluble portion and a water insoluble portion wherein the water insoluble portion includes the first and second organisms; and
    (iv) separating the water insoluble portion from the fermented mixture, thereby isolating the water soluble portion and producing the fermentation extract which consists of extra-cellular secretions from the simultaneous fermentation.

15. A method for stimulating the production of hyaluronic acid and CD44 in skin cells comprising contacting skin of a subject with the topical composition according to claim 1.

16. A method for stimulating the production of hyaluronic acid and Caspase-14 in skin cells comprising contacting skin of a subject with the topical composition according to claim 1.

17. The topical composition according to claim 1, wherein the dermatologically acceptable vehicle comprises emulsion carriers, anhydrous liquid solvents, aqueous-based single phase liquid solvents, or thickened versions of the anhydrous and aqueous-based single phase liquid solvents.

18. The topical composition according to claim 1, wherein the dermatologically acceptable vehicle comprises hydroalcoholic system or oil-in-water emulsion.

19. A process of preparing a fermentation extract from a simultaneous fermentation, the process comprising:
 (i) growing a first organism to a late-logarithmic growth phase using a first chemically defined nutrient media to produce a second nutrient media containing the first organism and secondary extracellular metabolites expressed from the first organism;
 (ii) contacting the second nutrient media with a second organism;
 (iii) allowing the first organism and the second organism to be fermented simultaneously in the second nutrient media in order to produce a fermented mixture containing a water soluble portion and a water insoluble portion wherein the water insoluble portion includes the first and second organisms; and
 (iv) separating the water insoluble portion from the fermented mixture, thereby isolating the water soluble portion and producing the fermentation extract consisting of extra-cellular secretions from the simultaneous fermentation,
 wherein the first microorganism is selected from the group consisting of the family Propionibacteriaceae and micro-algae, wherein the micro-algae is selected from the group consisting of Thraustochytid and *Ulkenia* sp., and the second organism is of the family Lactobacillaceae.

20. The process according to claim 19, wherein the first organism and the second organism are grown simultaneously under aerobic or anaerobic conditions.

* * * * *